(12) United States Patent
Czaplewski-Campbell et al.

(10) Patent No.: US 11,617,519 B2
(45) Date of Patent: Apr. 4, 2023

(54) NEEDLE ELECTRODE FOR POSITION-DEPENDENT INJECTION

(71) Applicant: International Business Machines Corporation, Armonk, NY (US)

(72) Inventors: Sarah K. Czaplewski-Campbell, Rochester, MN (US); Eric J. Campbell, Rochester, MN (US); Jennifer I. Bennett, Rochester, MN (US); Elin F. LaBreck, Rochester, MN (US); Christopher Steffen, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 719 days.

(21) Appl. No.: 16/577,738

(22) Filed: Sep. 20, 2019

(65) Prior Publication Data

US 2021/0085212 A1 Mar. 25, 2021

(51) Int. Cl.
*A61B 5/00* (2006.01)
*A61B 5/06* (2006.01)
(Continued)

(52) U.S. Cl.
CPC ............ *A61B 5/068* (2013.01); *A61B 5/0538* (2013.01); *A61B 5/4839* (2013.01);
(Continued)

(58) Field of Classification Search
CPC ....... A61B 5/0538; A61B 5/068; A61B 5/283; A61B 5/4839; A61B 5/6848;
(Continued)

(56) References Cited

U.S. PATENT DOCUMENTS

| 5,271,413 A | 12/1993 | Dalamagas et al. |
| 6,440,118 B2 | 8/2002 | Burr et al. |

(Continued)

FOREIGN PATENT DOCUMENTS

| EP | 2978370 B1 | 5/2019 |
| WO | 2014016765 A2 | 1/2014 |
| WO | 2015017409 A1 | 2/2015 |

OTHER PUBLICATIONS

Kalvoy et al., "Impedance-based tissue discrimination for needle guidance," Physiological Measurement, 30, 2009, pp. 129-140, IOP Publishing, DOI: 10.1088.0967-334/30/2/002.

(Continued)

*Primary Examiner* — Mark D Remaly
(74) *Attorney, Agent, or Firm* — Kelsey M. Skodje

(57) ABSTRACT

A device includes a syringe, which has a tip, plunger, and barrel containing a fluid. The device also includes a needle electrode coupled to the tip of the syringe, a release component, and a control component configured to receive electrical measurements made by the needle electrode, determine impedance values from the electrical measurements, and identify a target tissue based on the impedance values. In response to the identification, the control component generates instructions to reposition a release component. A method includes receiving electrical measurements from a needle electrode, determining impedance values based on the electrical measurements. A target tissue is identified based on the impedance values, and a release component is repositioned in response. An article of manufacture includes a needle electrode and a microprocessor configured to receive electrical measurements, determine impedance values, identify a target tissue based on the impedance values, and generate instructions to reposition a release component.

12 Claims, 2 Drawing Sheets

(51) Int. Cl.
*A61B 5/0538* (2021.01)
*A61M 5/31* (2006.01)
*A61M 5/32* (2006.01)
*A61B 5/283* (2021.01)

(52) U.S. Cl.
CPC ......... *A61B 5/6848* (2013.01); *A61M 5/3129* (2013.01); *A61B 5/283* (2021.01); *A61B 5/6885* (2013.01); *A61M 5/3148* (2013.01); *A61M 5/32* (2013.01)

(58) Field of Classification Search
CPC ..... A61B 5/6885; A61M 5/20; A61M 5/3129; A61M 5/3148; A61M 5/32; A61M 5/329; A61M 5/42; A61M 5/427; A61M 5/46
See application file for complete search history.

(56) References Cited

U.S. PATENT DOCUMENTS

| | | |
|---|---|---|
| 7,328,065 B2 | 2/2008 | Watanabe et al. |
| 8,027,740 B2 | 9/2011 | Altman et al. |
| 8,177,748 B1 | 5/2012 | Beyerlein |
| 2001/0049510 A1* | 12/2001 | Burr ................. A61B 5/053 604/272 |
| 2005/0215945 A1 | 9/2005 | Harris et al. |
| 2014/0364797 A1 | 12/2014 | Schoenbach et al. |
| 2019/0030329 A1* | 1/2019 | Hannaman ........ A61M 5/31568 |

OTHER PUBLICATIONS

"A Technology Solution to Discriminate Between Tissue and Blood," Innocentive.com, Theoretical-Licensing Challenge, Posted Nov. 11, 2016, 2 pages. https://www.innocentive.com/ar/challenge/9933941.

Faes et al., "The electric resistivity of human tissues (100 Hz-10 MHz): a meta-analysis of review studies," Physiological Measurement, 20, Dec. 1999, pp. 1-10, DOI: 10.1088/0967-3334/20/4/201.

"Quick-Core® Biopsy Needle," Cook Medical, printed Sep. 20, 2019, 4 pages. https://www.cookmedical.com/products/ir_qct_webds/.

* cited by examiner

NEEDLE ELECTRODE FOR POSITION-DEPENDENT INJECTION

BACKGROUND

The present disclosure relates to needle-based injection and, more specifically, to injection at a target tissue.

Various types of biological tissues have different electrical properties. Electrodes can be used to distinguish between different tissues by measuring impedance. For example, electrodes inserted into biological tissue can distinguish between muscle and subcutaneous tissues because of their differences in impedance. Electrodes can therefore have applications in guiding clinical equipment through biological tissues during invasive procedures. For example, electrode needle probes can help guide placement of cannulas and catheters.

SUMMARY

Various embodiments are directed to a device. The device includes a syringe, which has a tip, plunger, and barrel containing a fluid. The device also includes a needle electrode coupled to the tip of the syringe. The needle electrode can have a coaxial structure that includes a first conductive layer comprising a hollow needle (e.g., a stainless steel needle), a dielectric layer that coats an outer surface of the hollow needle, and a second conductive layer that coats an outer surface of the dielectric layer. Further, the device includes a release component, which can be repositioned to allow the fluid to exit the barrel, and a control component. The control component is configured to receive electrical measurements made by the needle electrode, determine impedance values from the electrical measurements, and identify a target tissue based on the impedance values. In response to the identification, the control component generates instructions to reposition the release component. The control component can also generate instructions to automatically inject fluid into the target tissue. Further, the device can include a communication component, which can display impedance values on a display screen.

Additional embodiments are directed to a method of transferring a fluid. The method includes receiving electrical measurements from a needle electrode. The needle electrode can have a coaxial structure with a first conductive layer comprising a hollow needle, a dielectric layer coating an outer surface of the hollow needle, and a second conductive layer coating an outer surface of the dielectric layer. The method also includes determining impedance values based on the electrical measurements. The impedance values can be determined in real time, and can be displayed on a user interface. A target tissue is identified based on the impedance values, and a release component is repositioned in response to the identification. A notification, such as an audible alert, can also be generated in response to the identification. In response to the repositioning, the fluid can be injected through the needle electrode into the target tissue.

Further embodiments are directed to an article of manufacture, which includes a needle electrode electrically connected to a microprocessor. The needle electrode can have a coaxial structure, and can be coupled to a syringe. The microprocessor is configured to receive electrical measurements from the needle electrode, determine impedance values based on the electrical measurements, identify a target tissue based on the impedance values, and generate instructions to reposition a release component (e.g., a valve) in response to the identification of the target tissue.

DETAILED DESCRIPTION

Figure 1A:
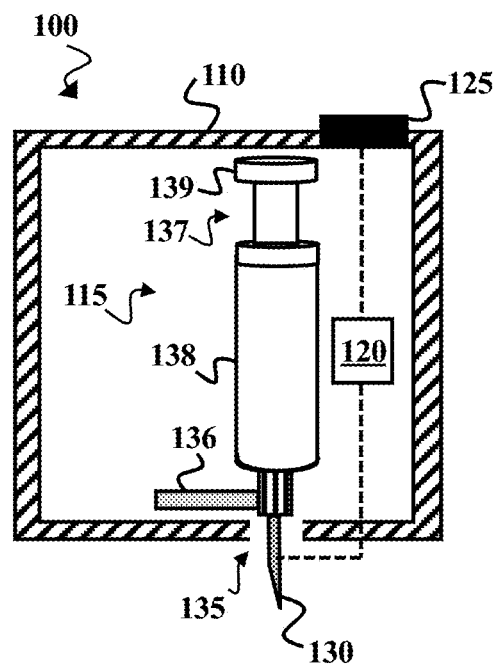
FIGS. 1A and 1B are schematic diagrams illustrating an injection assembly and a needle electrode environment, according to some embodiments of the present disclosure.

Various procedures involve insertion of hollow needles (e.g., hypodermic needles) into biological tissue. For example, syringes having hypodermic needles ("hypodermic syringes") are used to obtain samples of blood and other tissues (e.g., for biopsies). Hypodermic syringes are also used to inject antibiotics and other medications, vaccines, contrast agents, etc. Common types of injections involve injecting a fluid directly into subcutaneous tissue (subcutaneous injections), veins (intravenous injections), muscle tissue (intramuscular injections), or the dermis (intradermal injections). Additional examples involving the use of hollow needles in biological tissue and other materials are discussed in greater detail below.

It important to determine the position of a needle after it has been inserted. Injection sites are selected based on the purpose of the injection, the material being injected, and tissue characteristics at the injection site. For example, muscle tissue has larger and more numerous blood vessels than subcutaneous tissue. Therefore, materials injected directly into muscle tissue typically enter the blood stream more quickly than fluids injected into subcutaneous tissue. Therefore, vaccines are generally injected intramuscularly because subcutaneous injection would result in slow antigen mobilization and processing. In contrast, insulin injections are administered subcutaneously because injection directly into muscle would cause the insulin to be used too quickly, resulting in dangerously low blood glucose levels.

Techniques for determining a needle's location include aspiration, which involves determining whether the needle has entered a blood vessel by drawing a small amount of fluid from tissue penetrated by the needle. The presence of blood in the fluid is an indicator that the needle has reached a blood vessel. However, this is less useful when the intended target of the needle is not a blood vessel, and in some instances, blood can enter the fluid even when the needle is not properly inserted into a blood vessel. Additionally, the aspiration technique is time consuming and difficult, and improper techniques can result in injuries. Another technique for needle placement involves determining the depth of an inserted needle. However, this method can be unreliable because there is considerable variation in the depth of biological tissues across different injection sites and different individuals.

Further, many injections are administered using autoinjectors having buttons that, when pressed, cause the needle of a spring-loaded syringe to automatically puncture the skin and inject a preloaded fluid. Autoinjectors can be stored and transported easily, and rapidly deployed. Therefore, autoinjectors are often used by non-medical professionals to self-administer pharmacological agents, such as epinephrine, insulin, and antidotes (e.g., atropine). However, the simplicity and speed with which autoinjectors can be used can result in accidental injections at the wrong locations and/or dosages.

A technique and apparatus for safe administration of injections into target tissues are disclosed. A target tissue (e.g., muscle) is selected before injecting a fluid (e.g., a fluid containing a pharmacological agent) into the tissue. The needle of a syringe containing the material is then used to locate and penetrate the target tissue. The needle is a needle electrode having a coaxial structure for accurately identifying tissue based on impedance. The coaxial structure includes two conductive layers separated by an insulating layer. A mechanism coupled to the syringe prevents fluid from entering the needle unless the needle is embedded in the target tissue. This prevents accidental injection of the fluid into tissues other than the target tissue. It should also be understood that the disclosed technique and apparatus can be used for applications other than injection into biological tissue. This is discussed in greater detail below.

Figure 1B:
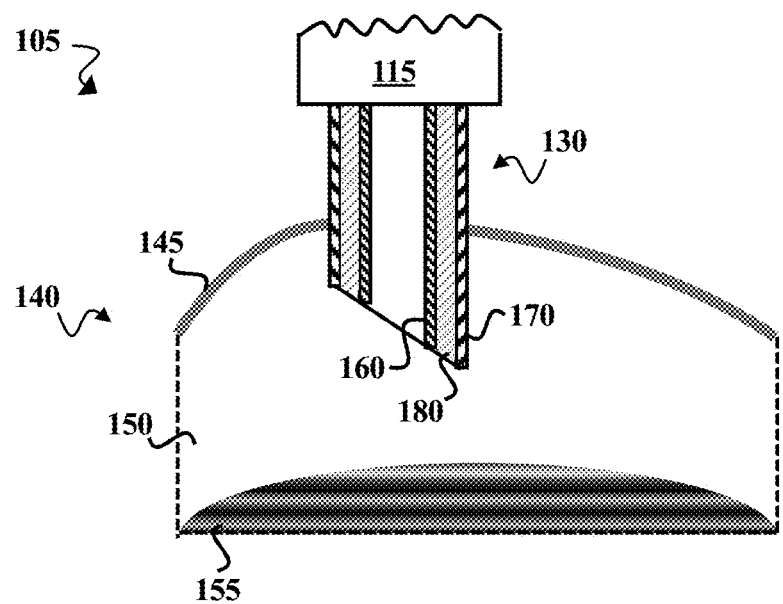

FIGS. 1A and 1B are schematic diagrams illustrating an injection assembly 100 and an injection environment 105, according to some embodiments of the present disclosure. The injection assembly 100 of FIG. 1A includes a housing 110 for a syringe 115, a control component 120, and a communication component 125. The assembly 100 also includes a needle electrode 130 (also referred to herein as "needle 130"), an aperture 135, and a release component 136.

The syringe 115 can be any appropriate syringe made from one or more materials such as glass, plastic, metal, etc. Syringes such as these, which are used in conjunction with hypodermic needles, are known to persons of ordinary skill in the art. The syringe 115 has a plunger 137 and a barrel 138. The tip of the barrel 138 is fitted to the hub of the needle 130. The plunger has a first end 139, which protrudes out of the barrel of the syringe 115, and a second end (not shown), which extends into the barrel 138. The syringe 115, control component 120, and/or needle electrode 130 can be at least partially enclosed in the housing 110, which provides protection from physical damage. Examples of housing 110 enclosure materials that can be used include plastics (e.g., poly(methyl methacrylate), polyvinyl chloride, polystyrene, etc.), glass, ceramics, steel, aluminum, cermets, etc.

The housing 110 has an aperture 135 (e.g., slot or hole) to allow the needle 130, and optionally a portion of the barrel 138 (e.g., the tip), to extend out of the housing 110. The needle 130 and/or aperture 135 can be capped when not in use. There can be additional apertures (not shown) in the housing 110, such as apertures that allow access to the syringe 115 (e.g., to press the plunger 137 and/or remove the syringe 115 from the housing 110), the communication component 125, and/or other components (e.g., microcontrollers, microprocessors, flash memory components, power supplies, motors, etc.). Additionally, in some embodiments the housing 110 can be opened in order to access these components. In some embodiments, the needle 130 is enclosed within the housing 110 when not in use. When an injection or impedance measurement is to be carried out, the syringe 115 and needle 130 are moved toward the aperture 135, manually or automatically, until the needle 130 is sufficiently extended to puncture the biological tissue injection target (see, e.g., FIG. 1B).

In some instances, the only portion of the syringe 115 enclosed by the housing 110 is the barrel 138. For example, the control component 120 can be mechanically connected to the outer surface of the barrel 138, and surrounded by the housing 110. The syringe 115 and/or needle electrode 130 can optionally be removed from the housing 110 and replaced. In some embodiments, the needle 130 can be non-releasably coupled to the housing 110, while the syringe 115 can be removed and either replaced with a new syringe or cleaned and put back into the housing 110. In other embodiments, the syringe 115 is non-releasably coupled to the housing 110, while the needle 130 can be replaced.

The control component 120 includes a microprocessor (e.g., a microcontroller) that receives electrical measurements from the needle electrode 130 via conductive connectors (not shown) such as wires and/or conductive adhesive. The control component 120 determines impedance characteristics from these measurements. Impedance characteristics are values based on electrical signals that indicate the impedance of a type of tissue. For example, impedance can be computed from frequency-dependent capacitance and resistance. Impedance is a complex number, and its real part is resistance. Herein, "impedance characteristics" and "impedance values" refer to materials' resistivity unless specified otherwise. The control component 120 analyzes the impedance of a biological tissue to determine whether it matches a known impedance value or range of values (e.g., a resistivity characteristic of subcutaneous tissue or of muscle tissue). This is discussed in greater detail with respect to FIGS. 1B and 2.

The control component 120 also instructs the communication component 125 to convey information regarding these values. The communication component 125 can include a display screen (e.g., a liquid crystal display (LCD), light-emitting diode (LED), or gas plasma panel) that displays text and/or graphical images. For example, the communication component 125 can display impedance values or the names of identified biological tissues (e.g., "subcutaneous tissue" or "muscle") on a display screen embedded in the housing 110. In other embodiments, the communication component 125 is a text and/or graphical image display screen on an external device (e.g., a desktop computer, laptop computer, mobile computing device, etc.) in communication with the assembly 100. The communication component 125 can also provide audible alerts (e.g., a beep or buzz) and/or lights that turn on, turn off, and/or change color in response to specified impedance values.

In some embodiments, the communication component 125 does not show text or graphical images on a display screen. For example, the communication component 125 may not include a display screen. In these instances, the communication component 125 can have a light or sound alert indicating that a selected impedance value has been reached, as well as a mechanical button, switch, slider bar, etc. with which a user can send instructions to the controller component 120 (e.g., instructions to identify a selected biological tissue, to turn the electronic components of the assembly 100 on and off, etc.). In other embodiments, instructions such as these are selected via a user interface on a touch-screen display. Additionally, the communication component 125 can send instructions to an instrument for carrying out automatic injections, such as a robotic arm.

The control component 120 can also direct fluid dispensation from the syringe 115. For example, the assembly 100 can include a motor (not shown), such as a stepper motor. When instructed to by the control component 120, the motor can cause a release component 136 to change position so that a fluid stored in the barrel 138 of the syringe 115 is able to travel into the needle 130. The release component 136 can be a valve or barrier coupled to the tip of the syringe 115 and positioned between the syringe 115 and needle 130 to block fluids in the barrel 138 from entering the needle 130. When the release component 136 is repositioned so that the valve is opened or the barrier is removed, fluid can be released through the hollow needle 130 when pressure is exerted on the first end 139 of the plunger 137 (e.g., manually or automatically).

However, any appropriate injection control mechanism can be used for the release component 136. In some embodiments, the release component 136 is not positioned between the syringe 115 and needle 130. For example, there can be a plunger lock (not shown) such as a barrier or clamp mechanically connected to the plunger 137. The plunger lock can be mounted on a sliding track. When the plunger lock is moved along the sliding track toward the syringe 115, the first end of the connected plunger 137 moves further into the barrel 138, causing fluid to enter the needle 130. The volume of fluid dispensed from the syringe 115 can be controlled by adjusting the distance the plunger lock is moved down the track.

Another type of plunger lock can prevent the plunger 137 from moving by gripping the plunger 137 with a clamp, or by stopping the first end 139 of the plunger 137 from moving past a given point by placing a barrier in its path. When fluid is to be dispensed, the control component 120 can direct the plunger lock to be released, allowing movement of the plunger 137 into the barrel 138 of the syringe 115 (e.g., manually or automatically). A plunger lock such as this can be used to control the volume of fluid dispensed as well. For example, the control component 120 can direct the motor to adjust the distance of the lock from the barrel 138 of the syringe 115 (e.g., by moving a barrier along a sliding track). The barrier can be positioned closer to the syringe 115 to increase the volume of fluid to be dispensed.

However, the release component 136 can be any component that prevents injection from occurring (e.g., a barrier stopping a spring from being released). The assembly 100 can also include various components that are not illustrated herein, such as additional microprocessors, power supplies, memory components, batteries and/or connections to an external power supply, capacitors, resistors, inductors, memristors, semiconductors, diodes, transistors, integrated circuits, wired links, wireless communication links, adaptors, and transducers. These and other conventional components of injection devices (e.g., autoinjectors) are known to persons of ordinary skill in the art.

The injection environment 105 is illustrated in FIG. 1B. To illustrate the injection environment 105, but not to limit embodiments, FIG. 1B is described within the context of the injection assembly 100 of FIG. 1A. Where elements described with respect to FIG. 1B are identical to elements shown in FIG. 1A, the same reference numbers are used in both Figures. However, it will be appreciated that various alternative arrangements can be used within the context of the injection environment 105.

FIG. 1B shows a partial view of the syringe 115 and a cross-sectional view of the needle electrode 130 embedded in a portion of biological tissue 140. The illustrated biological tissue portion 140 includes a first layer 145, a second layer 150, and a third layer 155. In this example, the first layer 145 is skin (e.g., epidermis and dermis), the second layer 150 is subcutaneous tissue, and the third layer 155 is muscle. The needle electrode 130 is illustrated as having punctured the epidermis and dermis of the skin 145 and entered the subcutaneous tissue 150.

The biological tissue portion 140 can include additional or alternative layers, depending upon the organism, injection site, length of the needle 130, depth of insertion, etc. Examples of layers can include various epithelia or other integumentary tissues, connective tissues (e.g., adipose tissue, cartilage, bone, blood, etc.), and nerve tissues. Layers can also include regions of abnormal or pathological tissue, such as benign or malignant lesions. Further, while animal tissues are illustrated herein, the biological tissue portion 140 can be from a plant. In some embodiments, at least one layer can be a synthetic material.

The needle electrode 130 has a coaxial structure with two conductive layers separated by a dielectric layer. The first (inner) conductive layer is a hollow needle 160. The hollow needle 160 can be any conventional conductive hollow needle, such as a hypodermic needle. The hollow needle 160 has an elongated hollow shaft having a first end and a second end. The first end of the shaft is coupled to a hub, which is fitted to the tip of the syringe 115, and the second end is a sharpened point through which fluid can pass. The hollow needle 160 can be made of stainless steel, though other conductive needle materials can be used in some embodiments (e.g., carbon steel, titanium, conductive polymer, titanium, gold, aluminum, copper, silver, etc.).

The exterior surface of the hollow needle 160 shaft is coated with the dielectric layer 180. The dielectric layer 180 is made of an insulating material, such as an insulating polymer or insulating enamel. Examples of insulating materials that can be used can include heat curing epoxy resins, polyimides, polytetrafluoroethylene, oxides of aluminum, titanium, and/or yttrium, glass, etc. The second (outer) conductive layer 170 coats the outer surface of the dielectric layer 180, and is made of a conductive material such as a conductive polymer, titanium, gold, aluminum, copper, silver, etc. In some embodiments, the outer conductive layer 170 is a suspended silver enamel, though any appropriate conductive material can be used (e.g., conductive steel alloys, iron, etc.). The outer conductive layer 170 can coat all or a portion of the dielectric layer 180 surface. Metals in the outer conductive layer 170 can be applied in various ways, such as by vacuum-deposition, electroplating, or lithography. The thickness of each layer 160, 170, and 180 can be selected based on the type of materials, desired resolution, etc. Examples of possible layer thicknesses include ~0.1 nm-1 nm, ~1 nm-200 nm, ~200 nm-500 nm, ~0.5 μm-5 μm, ~5 μm-500 μm, etc.

The conductive layers 160 and 170 are each electrically connected to the control component 120 (e.g., by wire connectors and/or conductive adhesive). The dielectric layer 180 prevents the conductive layers 160 and 170 from coming into electrical contact with one another. When the needle electrode 130 is inserted into biological tissue, the electrical impedance of the surrounding tissue can be determined from measurements collected using the needle electrode 130. This is discussed in greater detail with respect to FIG. 2. In some embodiments, the needle 130 can have one or more additional layers (e.g., a second dielectric coating) covering all or part of the outer conductive layer 170 surface.

Figure 2:
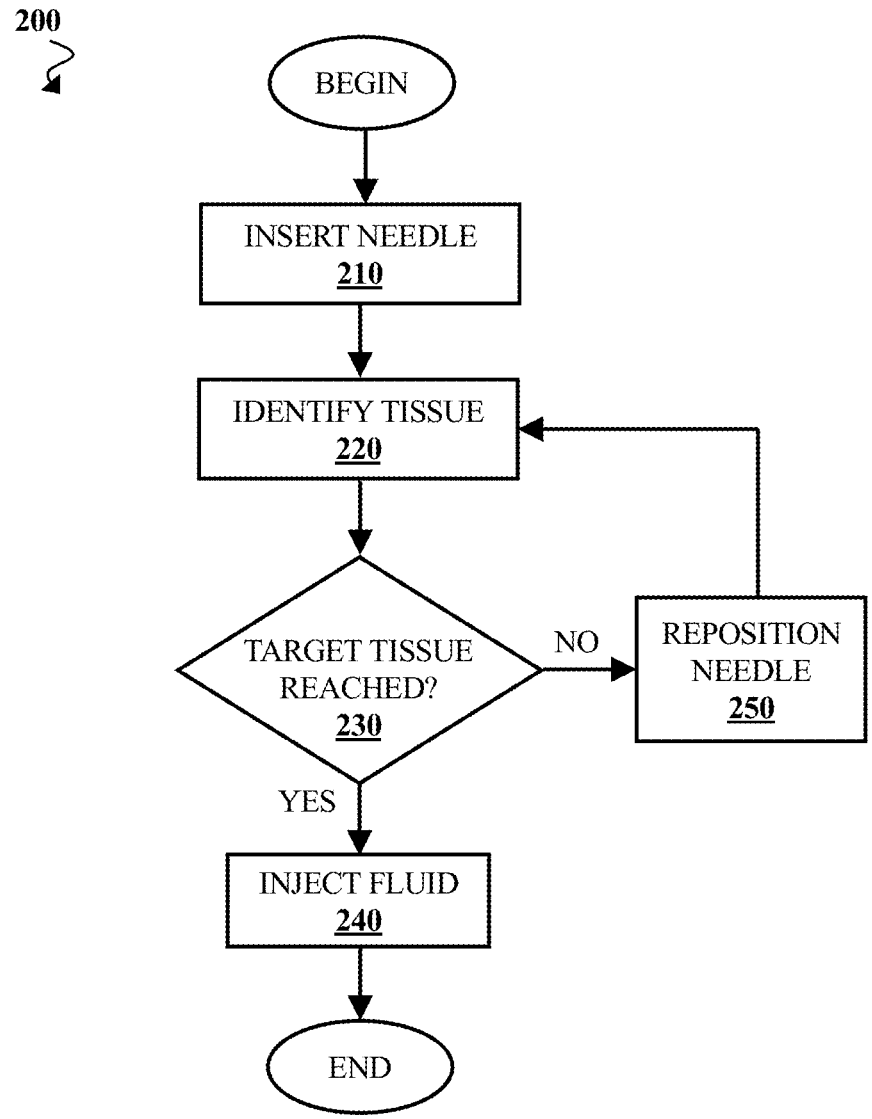
FIG. 2 is a schematic diagram illustrating a process of fluid injection, according to some embodiments of the present disclosure.

FIG. 2 is a schematic diagram illustrating a process 200 of fluid injection, according to some embodiments of the present disclosure. To illustrate process 200, but not to limit embodiments, FIG. 2 is described within the context of the injection assembly 100 of FIG. 1A and the injection environment 105 of FIG. 1B. Where elements described with respect to FIG. 2 are identical to elements shown in FIGS. 1A and 1B, the same reference numbers are used in both Figures. However, it will be appreciated that various alternative equipment arrangements can be used to perform process 200.

A needle electrode 130 is inserted into a biological tissue. This is illustrated at step 210. The placement of the needle 130 insertion depends upon the desired injection site and the type of injection. For example, in the tissue portion 140 illustrated in FIG. 1B, the needle 130 can be used to puncture the skin 145 of a person's upper arm, and inserted a short distance below the skin 145, when a subcutaneous injection is to be carried out. Alternatively, the needle 130 can be inserted more deeply if an intramuscular injection is to be carried out. The needle can be inserted by a person or a mechanical instrument (e.g., a robotic arm).

The identity of the tissue surrounding the inserted needle 130 is then determined. This is illustrated at step 220. The control component 120 makes this determination using electrical measurements collected via the needle electrode 130. However, in some embodiments the control component 120 sends the measurement data to an external computing device (e.g., a desktop computer, a laptop computer, a mobile computing device, etc.) for processing. The data can be sent via wires or wireless communication protocols (e.g., Wi-Fi). The control component 120 can be instructed to begin the measurements after the needle 130 has been inserted, though the measurements can begin prior to the insertion as well. These instructions can be entered through the communication component 125 (e.g., entered into a user interface, or by pressing a button or switch on the housing 110).

In order to measure impedance, the control component 120 or another electrical signal source applies a current (e.g., ~1 µA-10 µA) across the conductive layers 160 and 170 of the needle electrode 130. The frequency of the applied current depends upon the type of tissue at the injection site and/or other test parameters. Examples of frequencies at which measurements can be made can include ~100 Hz-100 kHz, ~10 kHz-50 kHz, ~20 kHz-50 kHz, ~5 kHz-200 kHz, ~20 kHz-100 kHz, ~100 kHz-500 kHz, ~5 kHz-1000 kHz, ~10 Hz-1 MHz, ~100 Hz-10 MHz, etc. However, any appropriate frequency range can be used (e.g., ~0.01 Hz-10 Hz, ~1 Hz-10 Hz, ~1 µHz-1 GHz, etc.).

The control component 120 then measures the voltage across the electrodes (conductive layers 160 and 170), and determines the impedance of the tissue around the needle electrode 130 in real time. In some embodiments, the measured tissue is the tissue in contact with the needle 130, or within a radius of about 100 nm-100 µm, though various radii are possible (e.g., ~100 µm-1 mm, ~1 mm-5 mm, ~5 mm-10 mm, ~10 mm-100 mm, etc.). The resolution of the impedance measurements can depend upon the surface area of the conductive layers 160 and 170, the distance between the conductive layers 160 and 170, the needle electrode 130 materials, the types of measurement equipment, the types of tissue, etc.

The control component 120 identifies the type of tissue surrounding the needle electrode 130 based on the impedance measurements. The control component 120 compares the impedance characteristics to known impedance characteristics in real time. For example, when a measured resistivity value matches (exactly or approximately) a known tissue resistivity, or falls within a known range of tissue resistivity values, the control component identifies the tissue in contact with the needle electrode 130 as being the type of tissue associated with the known resistivity.

For example, the resistivity of human adipose tissue is about 38.5 Ω·m, and the resistivity of human skeletal muscle tissue is about 1.71 Ω·m. Therefore, an impedance measurement of the subcutaneous layer 150 of the tissue portion 140 illustrated in FIG. 1B may detect a resistivity of approximately 38.5 Ω·m because subcutaneous tissue is largely composed of adipocytes. However, if the needle 130 is inserted deep enough to penetrate the muscle layer 155, the measured resistivity can be approximately 1.71 Ω·m. In some embodiments, types of tissue can have user-selected or preset ranges of resistivity values (e.g., ~1.00 Ω·m-2.50 Ω·m for skeletal muscle). Impedance values and/or tissue identifiers determined by the controller component 120 can be displayed on the communication component 125.

It is then determined whether the identified tissue is the target of the injection. This is illustrated at step 230. The injection target can be automatically identified by the control component 120 based on a preset or user-entered tissue selection. For example, if a user selects an option for intramuscular injection, the control component 120 can determine that the target tissue has been reached when an impedance characteristic of muscle tissue is detected (e.g., a resistivity value within a range of about 1.50 Ω·m-2.00 Ω·m). When the target tissue is identified, the communication component 125 can convey this information to a user (e.g., by displaying a textual or graphical indicator on a user interface, by turning on a light, by making a sound, etc.).

However, the injection target can also be identified by a user. For example, in some embodiments there is no preset or user-selected target. Instead, the user can determine that the target of an intramuscular injection has been reached when the communication component 125 indicates that the needle 130 has entered muscle tissue (e.g., by a message on a display screen). The user may also recognize the tissue location based on an impedance value displayed on a display screen. The user can then communicate to the control component 120 that the target tissue has been reached. For example, the user can press a button on the housing 110 upon determining that the needle 130 has penetrated the target tissue.

If the target tissue has been reached, fluid from the syringe 115 is injected into the tissue. This is illustrated at step 240. Until the control component 120 determines that the needle 130 is positioned within the target tissue, fluid is prevented from exiting the barrel 138 of the syringe 115 by the release component 136. However, when the target tissue has been reached, the release component 136 is repositioned to allow fluid to exit the syringe 115 through the needle 130. In some embodiments, the release component 136 is automatically repositioned by the control component 120. In other embodiments, the user can enter instructions via the communication component 125 to reposition the release component 136, or can manually reposition the release component 136.

In some embodiments, the communication component 125 indicates that the release component 136 has been repositioned to allow fluid injection, such as by displaying a textual or graphical indicator, turning on a light, making a sound, etc. The user can then cause pressure to be exerted on the plunger 137 of the syringe 115 (e.g., manually or via the communication component 125) to inject fluid into the target tissue. Alternatively, the plunger 137 can be automatically pressed, such as by a housing component (not shown) driven by a motor. In these instances, the communication component 125 can optionally indicate that the repositioning and/or injection has occurred. The communication component 125 can optionally request confirmation from a user before repositioning the release component 136 and/or injecting the fluid. However, the plunger 137 can be automatically pressed to inject the fluid without user intervention in other embodiments.

If the target tissue has not been reached, the needle 130 is repositioned. This is illustrated at step 250. In some embodiments, the needle 130 is repositioned manually by a user operating injection assembly 100. However, the needle 130 can also be repositioned by a mechanical instrument such as a robotic arm. The control component 120 continues to measure impedance and identify tissues, as illustrated at step 220, while the needle 130 is being repositioned. This can continue until the target tissue is identified, at which point the fluid is injected (step 240), or until the control component 120 receives instructions to stop collecting data.

The examples discussed herein and represented in the accompanying drawings may make reference to particular details. However, it will be understood that there are various modifications that can be made while retaining the spirit and scope of the disclosure. These would be easily recognized and carried out by one of ordinary skill in the art. For example, while the examples provided herein relate to fluid injection, assembly 100 can be used to withdraw materials (e.g., to draw blood or take biopsies), or to differentiate between tissues for other purposes (e.g., analytical or surgical). In some embodiments, the fluid is a liquid. However, the fluid can also be a gas or a mixture of liquid and gas. The needle 130 insertions into biological tissue can take place in vivo or ex vivo. Further, while biological tissues are described herein, assembly 100 can be used to distinguish between any materials having impedance variations that can be measured by the needle electrode 130 (e.g., soil, synthetic polymers, etc.).

Further, the diagrams illustrated in FIGS. 1A and 1B are for ease of description only, and are not to scale. Any appropriate size, shape, or arrangement of components known in the art can be used. Additionally, spatially relative terms used herein (e.g., "above," "below," "over," "under," etc.) are used to provide relative relationships between structures, and are intended to encompass various orientations of the assemblies. The use of these terms does not require a particular structure to be located in a particular location. Ranges (e.g., time, concentration, temperature, etc.) indicated herein include both endpoints and all numbers between the endpoints. Unless specified otherwise, the use of modifying terms such as "about", "approximately", or a tilde (~) in connection to a range applies to both ends of the range (e.g., "approximately 1 g-5 g" should be interpreted as "approximately 1 g-approximately 5 g"). As used herein, these modifying terms indicate +/−10% of a recited value, range of values, or endpoints of one or more ranges of values.

What is claimed is:

1. A device, comprising:
   a syringe having a tip, a plunger, and a barrel that contains a fluid;
   a needle electrode coupled to the tip of the syringe;
   a release component; and
   a control component configured to:
      receive an electrical measurement made by the needle electrode;
      determine an impedance value of the biological tissue from the electrical measurement using an electrical characteristic;
      identify a target tissue based on a computation using the impedance value; and
      in response to the identifying the target tissue, generate an instruction to reposition the release component.

2. The device of claim 1, wherein the repositioning of the release component allows the fluid to exit the barrel.

3. The device of claim 1, wherein the control component is further configured to generate instructions to automatically inject the fluid into the target tissue.

4. The device of claim 1, further comprising a communication component.

5. The device of claim 4, wherein the communication component displays impedance values on a display screen.

6. The device of claim 1, wherein the needle electrode has a coaxial structure comprising:
   a first conductive layer comprising a hollow needle;
   a coaxial dielectric layer coating an outer surface of the hollow needle; and
   a coaxial second conductive layer coating an outer surface of the dielectric layer.

7. The device of claim 6, wherein the hollow needle is a stainless steel needle.

8. The device of claim 1, wherein the electrical characteristic is selected from the group consisting of a frequency-dependent capacitance and a resistance.

9. An article of manufacture, comprising:
   a needle electrode electrically connected to a microprocessor, wherein the microprocessor is configured to:
      receive an electrical measurement made by the needle electrode;
      determine an impedance value of the biological tissue from the electrical measurement using an electrical characteristic;
      identify a target tissue based on a computation using the impedance value; and
      generate an instruction to reposition a release component in response to the identification of the target tissue.

10. The article of manufacture of claim 9, further comprising a syringe coupled to the needle electrode.

11. The article of manufacture of claim 9, wherein the release component is a valve.

12. The article of manufacture of claim 9, wherein the needle electrode has a coaxial structure.

* * * * *